United States Patent
Mitra et al.

(10) Patent No.: US 10,376,175 B2
(45) Date of Patent: Aug. 13, 2019

(54) SENSOR, SYSTEM, AND HOLDER ARRANGEMENT FOR BIOSIGNAL ACTIVITY MEASUREMENT

(71) Applicants: IMEC VZW, Leuven (BE); Stichting IMEC Nederland, Eindhoven (NL)

(72) Inventors: Srinjoy Mitra, Edinburg (GB); Bernard Grundlehner, Eindhoven (NL)

(73) Assignees: IMEC VZW, Leuven (BE); Stichting IMEC Nederland, Eindhoven (NL)

( * ) Notice: Subject to any disclaimer, the term of this patent is extended or adjusted under 35 U.S.C. 154(b) by 299 days.

(21) Appl. No.: 15/382,381

(22) Filed: Dec. 16, 2016

(65) Prior Publication Data

US 2017/0172447 A1  Jun. 22, 2017

(30) Foreign Application Priority Data

Dec. 22, 2015 (EP) ..................................... 15202202

(51) Int. Cl.
  *A61B 5/0478* (2006.01)
  *A61B 5/00* (2006.01)
(52) U.S. Cl.
  CPC .......... *A61B 5/0478* (2013.01); *A61B 5/0075* (2013.01); *A61B 5/0082* (2013.01);
  (Continued)
(58) Field of Classification Search
  CPC combination set(s) only.
  See application file for complete search history.

(56) References Cited

U.S. PATENT DOCUMENTS

2014/0018640 A1   1/2014  Udagawa et al.
2015/0223694 A1*  8/2015  Funane ................ A61B 5/1455
                                              600/407

(Continued)

OTHER PUBLICATIONS

Kamrani, Ehsan et al., "Low-Noise, High-Gain Transimpedance Amplifier Integrated With SiAPD for Low-Intensity Near-Infrared Light Detection", IEEE Sensors Journal, vol. 14, No. 1, Jan. 2014, 11 pages.

(Continued)

*Primary Examiner* — Scott Luan
(74) *Attorney, Agent, or Firm* — McDonnell Boehnen Hulbert & Berghoff LLP

(57) ABSTRACT

The disclosure relates to a sensor, a system, and a holder arrangement for biosignal activity measurement. One example embodiment includes a sensor module for brain activity measurement. The sensor module includes a main electrode base. The sensor module also includes a plurality of pins protruding from the main electrode base. The plurality of pins is arranged such that, when applied on a subject, the pins make contact with skin of the subject or are in close proximity with the skin of the subject. The main electrode base comprises electronic circuitry for near infrared spectroscopy (NIRS) measurements and electronic circuitry for electroencephalography (EEG) measurements, both connected to the plurality of pins. The plurality of pins includes electrically conductive pins. The plurality of pins also includes at least one source waveguide pin configured for light emitting purposes or at least one detector waveguide pin configured for light detection purposes.

12 Claims, 4 Drawing Sheets

(52) U.S. Cl.
CPC ...... *A61B 5/6814* (2013.01); *A61B 2562/066* (2013.01); *A61B 2562/16* (2013.01)

(56) References Cited

U.S. PATENT DOCUMENTS

2016/0120432 A1\* 5/2016 Sridhar ................ A61B 5/6898
 600/544
2017/0340260 A1\* 11/2017 Chowdhury ............. A61N 1/20

OTHER PUBLICATIONS

Safaie, J. et al., "Toward a Fully Integrated Wireless Wearable EEG-NIRS Bimodal Acquisition System", Journal of Neural Engineering, No. 10, 2013, pp. 1-11.

Sawan, Mohamed et al., "Wireless Recording Systems: From Non-invasive EEG-NIRS to Invasive EEG Devices", IEEE Transactions on Biomedical Circuits and Systems, vol. 7, No. 2, Apr. 2013, pp. 186-195.

Tzyy-Ping Jung, et al., "Concurrent EEG and NIRS Tomographic Imaging Based on Wearable Electro-optodes; Report to U.S. Army Research Office for research performed under federal grant at the University of California San Diego—La Jolla; Apr. 13, 2014", 27 pages.

\* cited by examiner

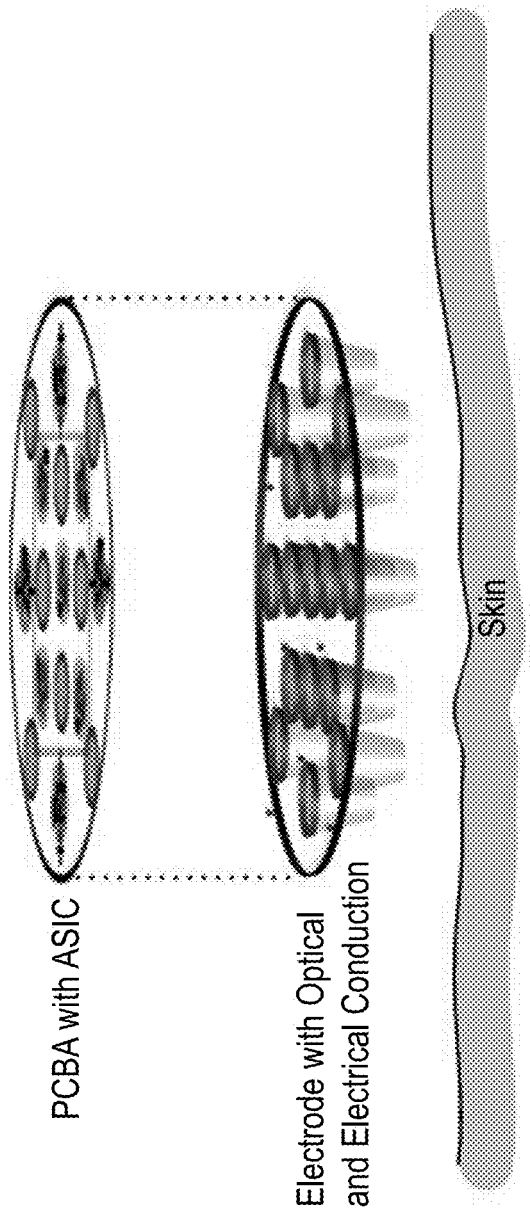

SENSOR, SYSTEM, AND HOLDER ARRANGEMENT FOR BIOSIGNAL ACTIVITY MEASUREMENT

CROSS-REFERENCE TO RELATED APPLICATIONS

The present application is a non-provisional patent application claiming priority to European Patent Application No. EP 15202202.6, filed Dec. 22, 2015, the contents of which are hereby incorporated by reference.

FIELD OF THE DISCLOSURE

The present disclosure relates to non-invasive biosignal activity measurement sensors and systems, including for example, brain activity measurement sensors and systems and more specifically to electroencephalogram (EEG) and near infrared spectroscopy (NIRS) sensors and systems for brain activity measurements.

BACKGROUND

There is currently an interest for the development of portable, lightweight and non-invasive biosignal activity measurement systems for monitoring biosignals and more specifically the neurophysiological activity of subjects in operational, clinical and research environments. For example, the simultaneous use of electroencephalographic (EEG) acquisition with functional near infrared spectroscopy (fNIRS) can provide a better understanding of the mechanisms involved in cerebral activation, since such techniques provide complementary information from the brain in terms of temporal and spatial resolution.

U.S. Patent Application 2014/0018640 A1, for example, describes a holder set and a brain function measuring device capable of executing measurements by an optical bioinstrumentation device (e.g. fNIRS) and by a an electroencephalograph (EEG) at the same time.

Report document "Concurrent EEG and NIRS tomographic imaging based on wearable electro-optodes", by Tzyy-Ping Jung et al., University of California—San Diego La Jolla, Apr. 13, 2014, describes a dual-modality neuroimaging system with EEG/NIRS electrodes, known as electro-optodes, that allow non-invasive and non-intrusive acquisition of EEG and fNIR signals. The developed brain activity sensor combines the capability of simultaneously recording both EEG and fNIRS signals from the same site by integrating both EEG electrode and NIR probe into one electro-optode.

SUMMARY

Some embodiments provide for a sensor module that can be applied, for example, to dual-modality EEG and fNIRS brain activity measurement.

The scope of the invention is defined by the claims.

According to example embodiments, there is provided a sensor module for biosignal activity measurement, comprising a main electrode base and a plurality of pins protruding from that main electrode base, configured such that, when applied on a subject, the pins make contact or are in close proximity to the subject's skin, and wherein the electrode base comprises electronic circuitry for biosignal measurement, wherein the electronic circuitry is connected to the plurality of pins; and the plurality of pins comprises pins that can conduct both light and electricity.

According to example embodiments, the plurality of pins comprises an outer electrically conductive surface or layer with an inner waveguide core.

According to example embodiments, the outer electrically conductive layer is a conductive mesh.

According to example embodiments, the conductive mesh comprises a woven fabric, comprising a plurality of conductive wires or fibers designed for being flexible and ensuring conductivity of the pins.

According to example embodiments, the inner core comprises a transparent silicone.

According to example embodiments, the plurality of pins comprises a material that can conduct both light and electricity.

According to example embodiments, there is provided a compact EEG and fNIRS sensor for brain activity measurement that may avoid the need for long connecting light fibers, costly lasers and large power supplies. According to an embodiment, the proposed EEG and fNIRS sensor may be integrated in a holder arrangement and communicate wirelessly with other sensors and/or system control modules, which allows for wearable applications and comfort during long term use. Also according to an embodiment, the EEG and fNIRS sensor may consume low power and be cheaper to implement.

According to an embodiment, there is provided a compact EEG and fNIRS sensor for brain activity measurement that can acquire fNIRS and EEG signals simultaneously, from the same brain region. Furthermore, according to an embodiment, the sensor module comprises a plurality of flexible pins for electrical conduction and/or light guidance that adapts to the scalp of a subject and allows for better quality measurements, where hair may block the light path. The pins separate hair and provide optical isolation.

According to example embodiments, there is provided a sensor module for brain activity measurement, comprising a main electrode base and a plurality of pins protruding from that main electrode base, configured such that, when applied on a subject, the pins make contact or are in close proximity to the subject's skin, and wherein the electrode base comprises electronic circuitry for NIRS and EEG measurement, wherein the electronic circuitry is connected to the plurality of pins; and the plurality of pins comprises a number of electrically conductive pins and at least one source waveguide pin configured for light emitting purposes and/or at least one detector waveguide pin configured for light detection purposes.

According to example embodiments, the electrical conductive pins are connected to EEG measurement circuitry and the at least one source and/or detector waveguide pins are connected to NIRS measurement circuitry.

According to example embodiments, the EEG and NIRS measurement circuitry is integrated in an ASIC located on a PCBA inside or connected to the electrode base.

According to example embodiments, the NIRS measurement circuitry comprises at least one light emitting circuit including a LED and at least one light detection circuit including a photo detector.

According to example embodiments, the photo detector is a Silicon Avalanche photo diode (SiAPD).

According to example embodiments, the NIRS measurement circuitry is configured for controlling the light emitting and detection circuits such as to create a plurality of source-detection pairs.

According to example embodiments, the plurality of pins comprises pins that can conduct both light and electricity and can be configured for EEG and/or NIRS measurement.

According to example embodiments, the plurality of pins comprises an outer electrically conductive surface or layer with an inner waveguide core.

According to example embodiments, the outer electrically conductive layer is a conductive mesh.

According to example embodiments, the conductive mesh comprises a woven fabric, comprising a plurality of conductive wires or fibers designed for being flexible and ensuring conductivity of the pins.

According to example embodiments, the inner core comprises a transparent silicone.

According to example embodiments, the plurality of pins comprises a material that can conduct both light and electricity.

The description also relates to an electrode holder for holding a plurality of sensors for brain activity measurement according to embodiments herein described.

The description also relates to a system comprising a plurality of sensors for brain activity measurement according embodiments herein described.

According to example embodiments, the system further comprises a control module configured for controlling activity and/or receiving measurements from the plurality of sensor modules.

According to example embodiments, the control module is further configured for controlling the light emitting and detection circuits of different sensor modules such as to create a plurality of source-detection pairs between light emitting circuits and light detection circuits located in different sensor modules.

Certain objects and advantages of various new and inventive aspects have been described above. It is to be understood that not necessarily all such objects or advantages may be achieved in accordance with any particular embodiment of the present invention as described in the claims. Those skilled in the art will recognize that the claims may be embodied or carried out in a manner that achieves or optimizes one advantage or group of advantages without necessarily achieving other objects or advantages.

BRIEF DESCRIPTION OF THE FIGURES

The above and other aspects of the sensor and system for brain activity measurement will be shown and explained with reference to the non-restrictive example embodiments described hereinafter.

FIG. 5 shows another perspective view of a sensor module for biosignal activity measurement, according to example embodiments.

DETAILED DESCRIPTION

In the following, in the description of example embodiments, various features may be grouped together in a single embodiment, figure, or description thereof for the purpose of streamlining the disclosure and aiding in the understanding of one or more of the various inventive aspects. This is however not to be interpreted as the invention requiring more features than the ones expressly recited in the independent claims. Furthermore, combinations of features of different embodiments and obvious known alternative structural means are meant to be within the scope of the present description, as would be clearly understood and derived by those skilled in the art. Additionally, in some examples, well-known methods, structures and techniques have not been shown in detail in order not to obscure the conciseness of the description.

Figure 1:
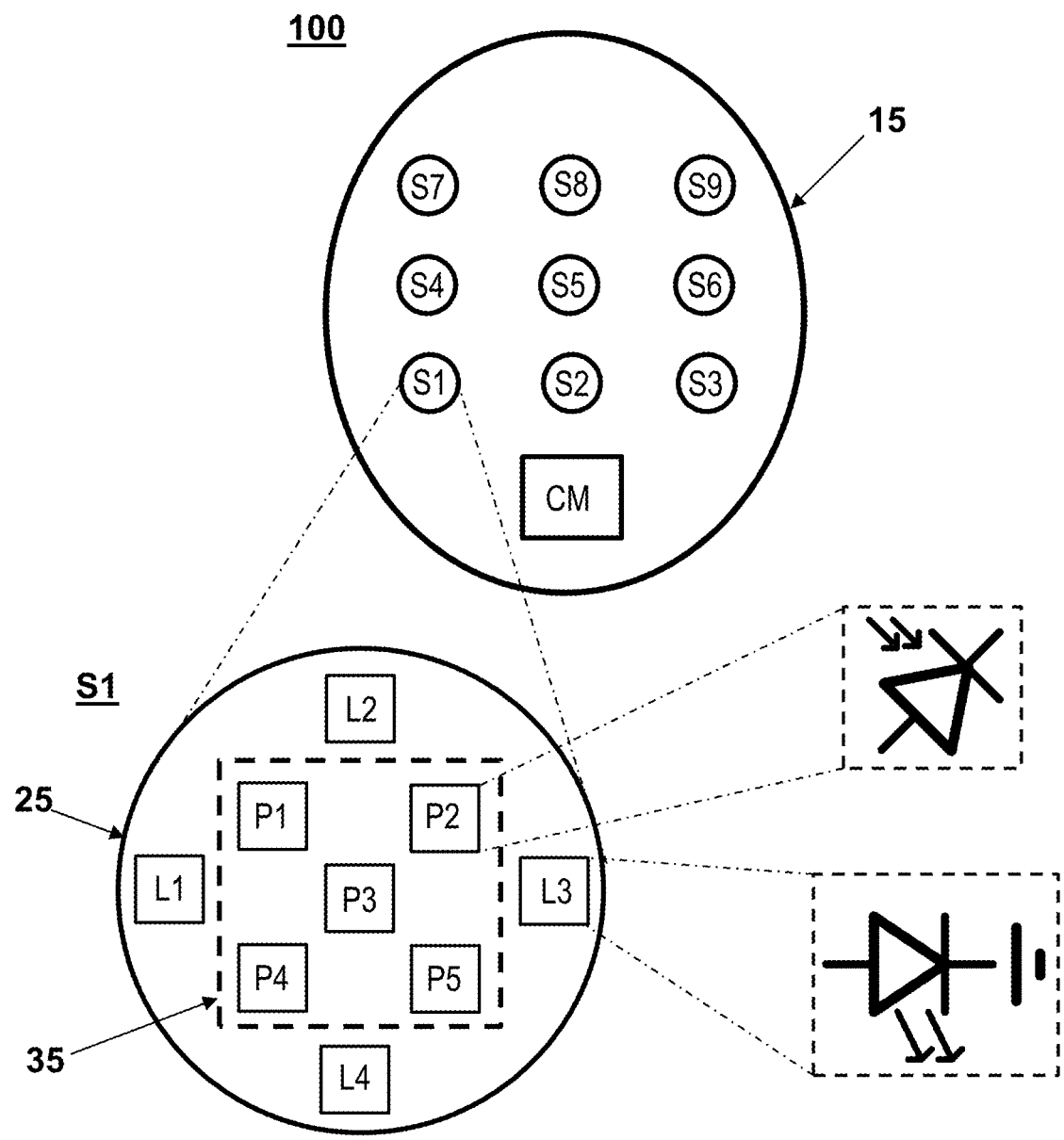
FIG. 1 shows a schematic of a system, a sensor holder set, and a sensor module for brain activity measurement, according to example embodiments.

FIG. 1 shows a schematic of a system 100, a sensor holder arrangement 15 and a sensor module S1 for brain activity measurement, according to example embodiments. The system 100 for brain activity measurement comprises a holder arrangement 15 so designed, configured and manufactured to be placed over the subject's head and to structurally hold a plurality of sensor modules S1 to S9 for brain activity measurement. The system 100 comprises a control module CM configured for controlling and/or receiving all the measurements from the plurality of sensor modules S1 to S9. In some embodiments, the control module CM may be located outside the sensor holder arrangement. Additionally or alternatively, at least some control functions of the control module CM may be located in the sensor holder arrangement 15. The plurality of sensor modules S1 to S9 may communicate between them and/or with the control module CM via electrical wired connections or wireless transmission. According to an embodiment, the control module CM may also perform signal processing techniques in order to quantify and/or improve the signal quality of the measurements received.

According to example embodiments, each sensor module, such as S1 in the figure, comprises a printed circuit board assembly (PCBA) 25, an application-specific integrated circuit (ASIC) 35, light emitting circuits L1 to L4 and light detection circuits P1 to P5. According to example embodiments, the ASIC 35 is mounted on the PCBA 25. According to an embodiment, the light emitting circuits L1 to L4 and the light detection circuits P1 to P5 are placed on the PCBA outside the ASIC. According to example embodiments, the light emitting circuits L1 to L4 comprise a light-emitting diode (LED) and the light detection circuits P1 to P5 comprise a photo detector such as a Silicon Avalanche photo diode (SiAPD). According to example embodiments, the ASIC uses low power and comprises high performance transimpedance amplifiers (TIA) which can reduce the size of NIRS sensing arrangement.

According to an embodiment, the ASIC comprises further electronic circuitry configured for modulating the light emitting sources (e.g. TDMA, CDMA) and for controlling the light emitting and detection circuits such as to create a plurality of source-detection pairs. According to example embodiments, the sensor module S1 is configured and operated such that at least one of the plurality of source-detection pairs presents a distance of at least 2 cm between the light source and the light detector, which would make one sensor module useful for fNIRS measurements. According to example embodiments, the ASIC 35 controls the light emitting sources according to compressive sampling (CS) techniques in order to further reduce power consumption. According to example embodiments, different sensor modules S1 to S9 are located at different locations of the subject's head and the system 100 is configured for controlling the light emitting and detection circuits of different sensor modules such as to create a plurality of source-detection pairs, which increases the depth of the optical path.

According to example embodiments, the PCBA 25 has a circular shape with a diameter in a range between 3 and 4 cm. According to example embodiments, the sensor module S1 further comprises biopotential sensors and electronic circuitry for EEG measurements and the ASIC 35 comprises processors for processing EEG and fNIRS signals.

According to example embodiments, the sensor modules S1 to S9 may not be isolated in different PCBAs, but their sensing circuitry may be located in one large PCBA made of a flexible material that is integrated in the holder arrangement 15.

Figure 2A:
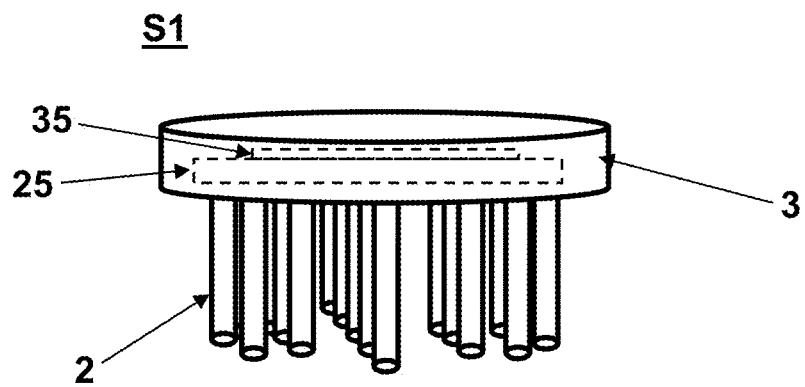
FIG. 2A shows a perspective view of an EEG and fNIRS sensor module for brain activity measurement, according to example embodiments.
Figure 2B:
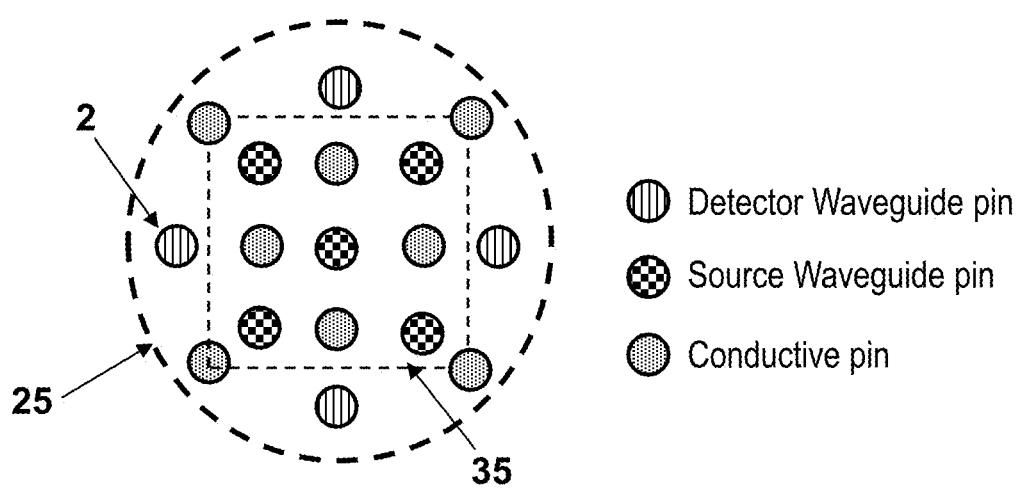
FIG. 2B shows a bottom view of an EEG and fNIRS sensor module for brain activity measurement, according to example embodiments.

FIG. 2A shows a perspective view of a dual modality sensor module S1 for biosignal activity measurement, according to example embodiments. The sensor module S1 comprises a main electrode body or base 3 and a plurality of pins 2 protruding from that main electrode base. The main electrode body or base 3 may serve both to hold the pins 2, the PCBA 25 and the ASIC 35 and to protect the PCBA and ASIC. According to example embodiments, the sensor module S1 comprises pins 2 with separate functionality. According to example embodiments, the sensor module S1 comprises: at least one source waveguide pin configured for light emitting purposes, at least one detector waveguide pin configured for light receiving/detection purposes, and a plurality of electrically conductive pins. According to example embodiments, the sensor module S1 comprises 17 pins: 4 detector waveguide pins, 5 source waveguide pins and 8 conductive pins, as is illustrated in FIG. 2B. According to example embodiments, the at least one detector waveguide pin is connected to a photo detector present on the PCBA 25, and the plurality of conductive pins are connected to light detection and biopotential circuitry respectively, integrated in the ASIC 35 and the at least one source waveguide pin is connected to light emitting circuitry present on the PCBA 25.

According to an embodiment, the ASIC 35 comprises circuitry for modulating the light emitting sources (e.g. TDMA, CDMA) and for controlling the light emitting and detection circuits such as to create a plurality of source-detection pairs. According to example embodiments, the sensor module S1 is configured and operated such that at least one of the plurality of source-detection pairs presents a distance of at least 2 cm between the light source and the light detector, which would make one sensor module useful for fNIRS measurements. According to example embodiments, the ASIC 35 comprises circuitry and processors for processing EEG and fNIRS signals.

According to an embodiment, the plurality of pins 2 protrude in the direction of the measurement surface or skin when the sensor module S1 is applied on the subject, e.g. an area of the subject's skin, for measurement purposes. The plurality of pins 2 are further configured to be flexible, which may aid in moving away hair and providing direct contact to the subject's scalp.

According to example embodiments, the sensor module S1 may incorporate the optical recording functionality along with the existing bio-potential recording.

Figure 3:
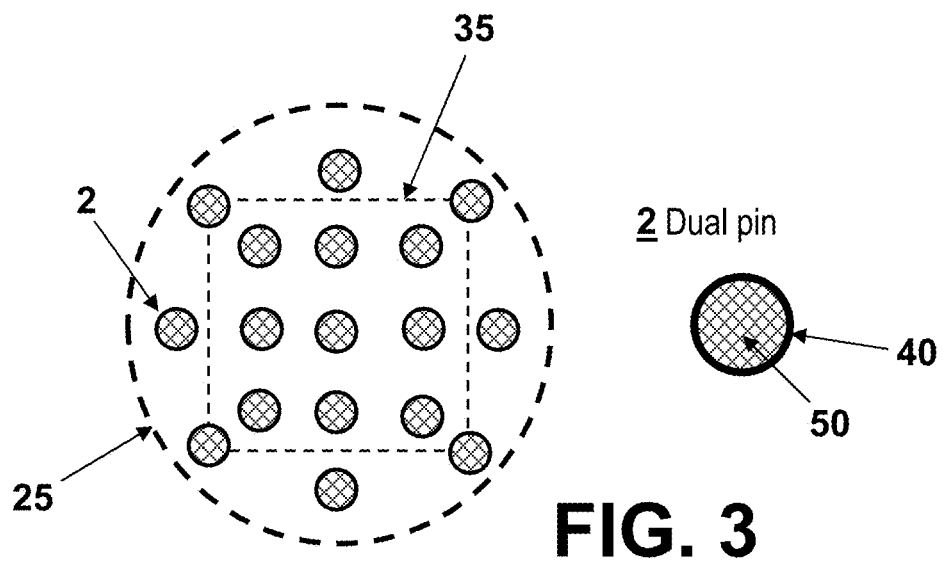
FIG. 3 shows a bottom view of a sensor module for biosignal activity measurement, according to example embodiments.

FIG. 3 shows a bottom view of a dual modality sensor module for biosignal activity measurement, according to example embodiments. In such embodiments, the sensor module S1 comprises a main electrode body or base 3 and a plurality of pins 2 protruding from that main electrode base as in FIGS. 2A and 2B, but the sensor module S1 comprises a plurality of pins with dual functionality, that is, such plurality of pins can conduct both light and electricity.

According to example embodiments, the pins 2 comprise an electrically conductive surface or outer layer material 40 with an inner waveguide core 50 or a core of a material that acts as a waveguide. According to example embodiments, the pins may be made by a core transparent silicone wrapped in a conductive fabric. According to example embodiments, the electrically conductive surface or fabric may be a conductive mesh.

According to example embodiments, the dual modality sensor module comprises circuitry, for example in the ASIC 35 or PCB 25, for configuring the dual modality pins for biosignal measurement, e.g. EEG and/or NIRS and/or other biosignals, such as ECG or PPG. It is understood that not all the pins of the sensor module shall be dual modality pins, but the sensor module may comprise both dual modality pins and single functionality or specialized pins.

Figure 4:
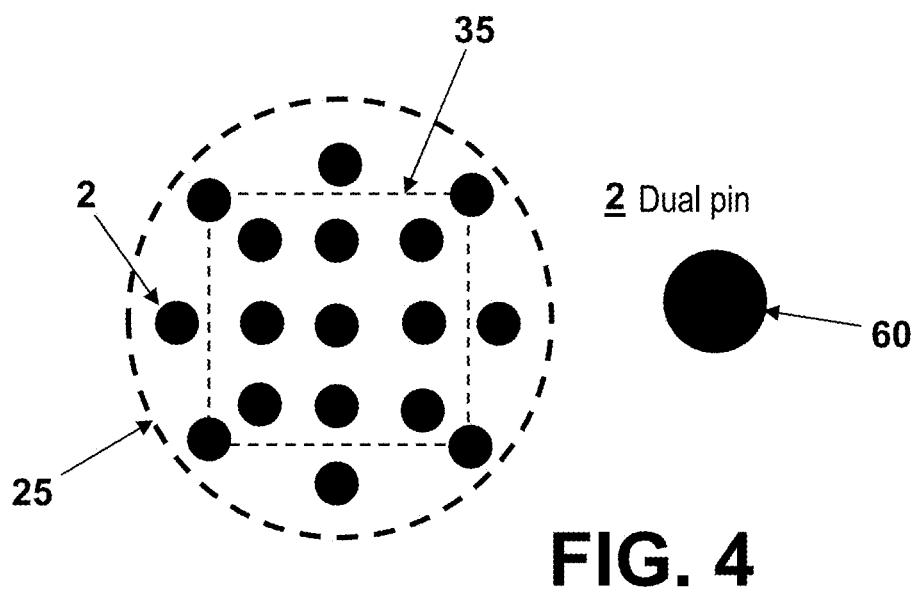
FIG. 4 shows a bottom view of a biosignal sensor module for brain activity measurement, according to example embodiments.

FIG. 4 shows a bottom view of a dual modality sensor module for biosignal activity measurement, according to example embodiments. In such embodiments, the sensor module S1 comprises a main electrode body or base 3 and a plurality of pins 2 protruding from that main electrode base as in FIGS. 2A and 2B, and the sensor module S1 comprises a plurality of pins with dual functionality, that is, such plurality of pins can conduct both light and electricity, but in this embodiment the pins are made from a material 60 that both guides light and is electrically conductive. According to an embodiment, the pins are made from an optically transparent silicone with added small metal or carbon particles.

FIG. 5 shows another perspective view of an EEG and NIRS sensor module for brain activity measurement, according to example embodiments, comprising the PCBA with ASIC and the electrodes with optical and electrical conductors.

What is claimed is:

1. A sensor module for brain activity measurement, comprising:
   a main electrode base; and
   a plurality of pins protruding from the main electrode base,
   wherein the plurality of pins is arranged such that, when applied on a subject, each pin of the plurality respectively makes contact with skin of the subject or is in close proximity with the skin of the subject,
   wherein the main electrode base comprises electronic circuitry for near infrared spectroscopy (NIRS) measurements and electronic circuitry for electroencephalography (EEG) measurements,
   wherein the electronic circuitry for NIRS measurements and the electronic circuitry for EEG measurements are connected to the plurality of pins,
   wherein the plurality of pins comprises pins that are respectively configured to conduct both light and electricity,
   wherein the pins configured to conduct both light and electricity each respectively include (i) an outer, electrically conductive layer and (ii) an inner waveguide core, and
   wherein the pins configured to conduct both light and electricity are configurable for NIRS measurements or EEG measurements.

2. The sensor module according to claim 1, wherein the inner waveguide core comprises a transparent silicone.

3. The sensor module according to claim 1, wherein the outer, electrically conductive layer is a conductive mesh.

4. The sensor module according to claim 3, wherein the conductive mesh comprises a woven fabric, and wherein the woven fabric comprises a plurality of conductive wires or fibers designed to be flexible and ensure conductivity of the pins configured to conduct both light and electricity.

5. The sensor module according to claim 1, wherein the sensor module is a component of a holder arrangement configured for being applied on a head of the subject.

6. The sensor module according to claim 1, wherein the sensor module is one of a plurality of sensor modules for brain activity measurement within a system.

7. The sensor module according to claim 6, wherein the system comprises a control module configured for controlling activity or receiving measurements from the plurality of sensor modules.

8. A sensor module for biosignal activity measurement, comprising:
a main electrode base; and
a plurality of pins protruding from the main electrode base,
wherein the plurality of pins is arranged such that, when applied on a subject, each pin of the plurality respectively makes contact with skin of the subject or is in close proximity with the skin of the subject,
wherein the main electrode base comprises electronic circuitry for biosignal measurement,
wherein the electronic circuitry is connected to the plurality of pins,
wherein the plurality of pins comprises pins that are respectively configured to conduct both light and electricity, and
wherein the pins configured to conduct both light and electricity each respectively include (i) an outer, electrically conductive layer and (ii) an inner waveguide core.

9. The sensor module according to claim 8, wherein the inner waveguide core comprises a transparent silicone.

10. The sensor module according to claim 8, wherein the outer, electrically conductive layer is a conductive mesh.

11. The sensor module according to claim 10, wherein the conductive mesh comprises a woven fabric, and wherein the woven fabric comprises a plurality of conductive wires or fibers designed to be flexible and ensure conductivity of the pins configured to conduct both light and electricity.

12. The sensor module according to claim 8, wherein the sensor module is a component of a holder arrangement configured for being applied on a head of the subject.

* * * * *